(12) United States Patent
Roche et al.

(10) Patent No.: US 11,723,777 B2
(45) Date of Patent: *Aug. 15, 2023

(54) PROSTHETIC DEVICES TO IMPROVE JOINT MECHANICS IN ARTHROPLASTY

(71) Applicant: Exactech, Inc., Gainesville, FL (US)

(72) Inventors: Christopher P. Roche, Gainesville, FL (US); Howard D. Routman, North Palm Beach, FL (US); Thomas W. Wright, Gainesville, FL (US); Corey Gaydos, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 214 days.

This patent is subject to a terminal disclaimer.

(21) Appl. No.: 17/039,648

(22) Filed: Sep. 30, 2020

(65) Prior Publication Data

US 2021/0154020 A1 May 27, 2021

Related U.S. Application Data

(63) Continuation of application No. 13/955,083, filed on Jul. 31, 2013, now Pat. No. 10,905,561.

(60) Provisional application No. 61/784,690, filed on Mar. 14, 2013, provisional application No. 61/678,353, filed on Aug. 1, 2012.

(51) Int. Cl.
*A61F 2/40* (2006.01)
*A61B 17/82* (2006.01)
*A61F 2/30* (2006.01)

(52) U.S. Cl.
CPC .......... *A61F 2/4081* (2013.01); *A61F 2/4059* (2013.01); *A61B 17/82* (2013.01); *A61F 2002/30332* (2013.01); *A61F 2002/30616* (2013.01); *A61F 2002/30729* (2013.01); *A61F 2002/407* (2013.01); *A61F 2002/4022* (2013.01); *A61F 2002/4066* (2013.01); *A61F 2002/4077* (2013.01)

(58) Field of Classification Search
CPC ............ A61F 2002/4011; A61F 2/4014; A61F 2/4059; A61F 2002/4062; A61F 2002/4066; A61F 2002/407; A61F 2002/4074; A61F 2/4081; A61F 2002/30616; A61F 2002/30614; A61F 2002/30607
See application file for complete search history.

(56) References Cited

U.S. PATENT DOCUMENTS 10,905,561 B2 * 2/2021 Roche .................. A61F 2/4081

* cited by examiner

*Primary Examiner* — Alvin J Stewart
(74) *Attorney, Agent, or Firm* — Greenberg Traurig, LLP

(57) ABSTRACT

Disclosed herein is a kit that includes a humeral stem having a central longitudinal axis, the humeral stem configured to attach to a resected bone; a first tuberosity component having a first thickness relative to the central longitudinal axis of the humeral stem; a second tuberosity component having a second thickness relative to the central longitudinal axis of the humeral stem, wherein the first thickness of the first tuberosity component is different than the second thickness of the second tuberosity component; and at least one proximal segment configured to engage at least one of the first tuberosity component and the second tuberosity component. In an embodiment, the first thickness of the first tuberosity component is at least 20 mm relative to the central axis of the humeral stem, and the second thickness of the second tuberosity component is at least 20 mm relative to the central axis of the humeral stem.

26 Claims, 21 Drawing Sheets

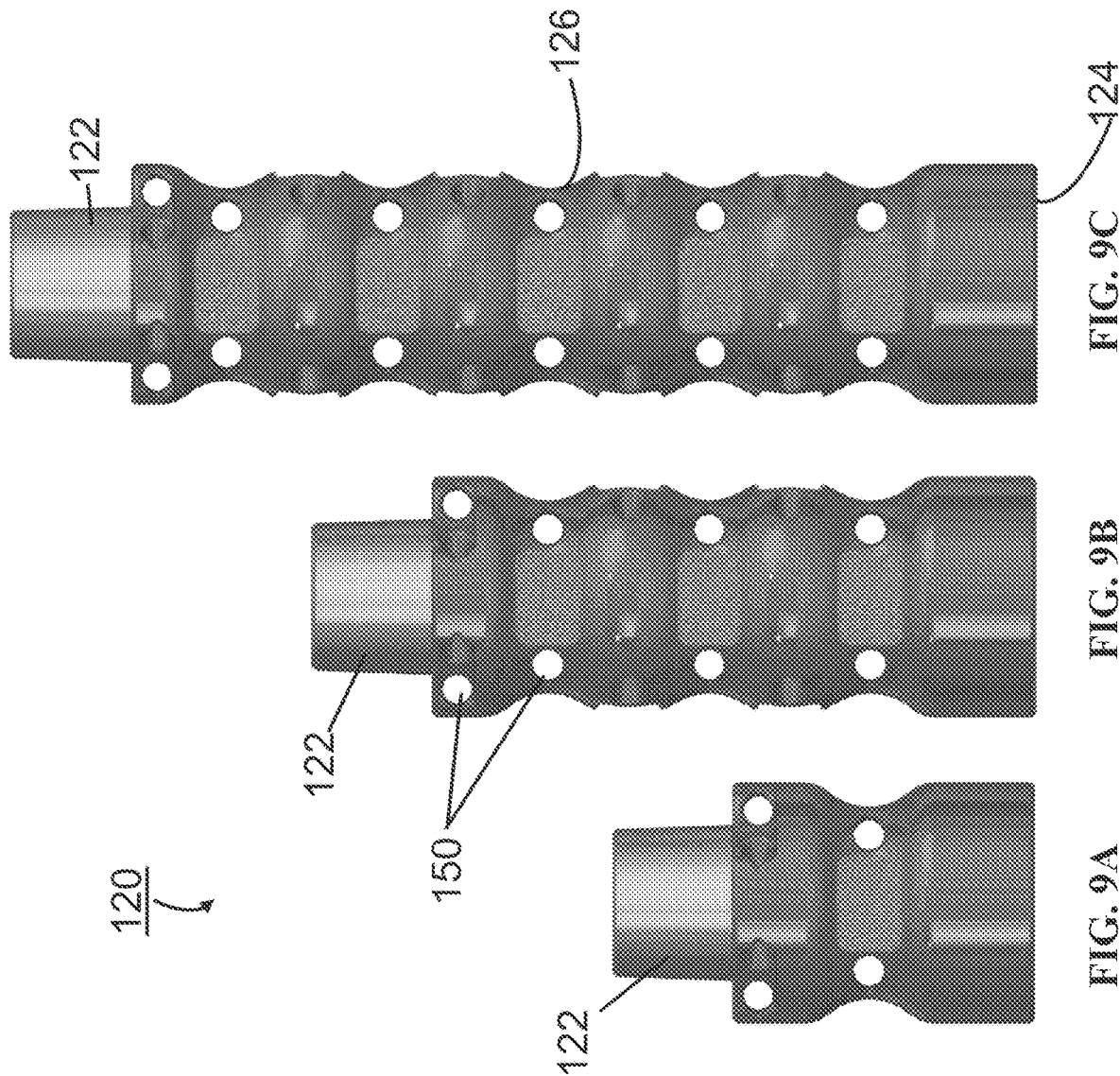

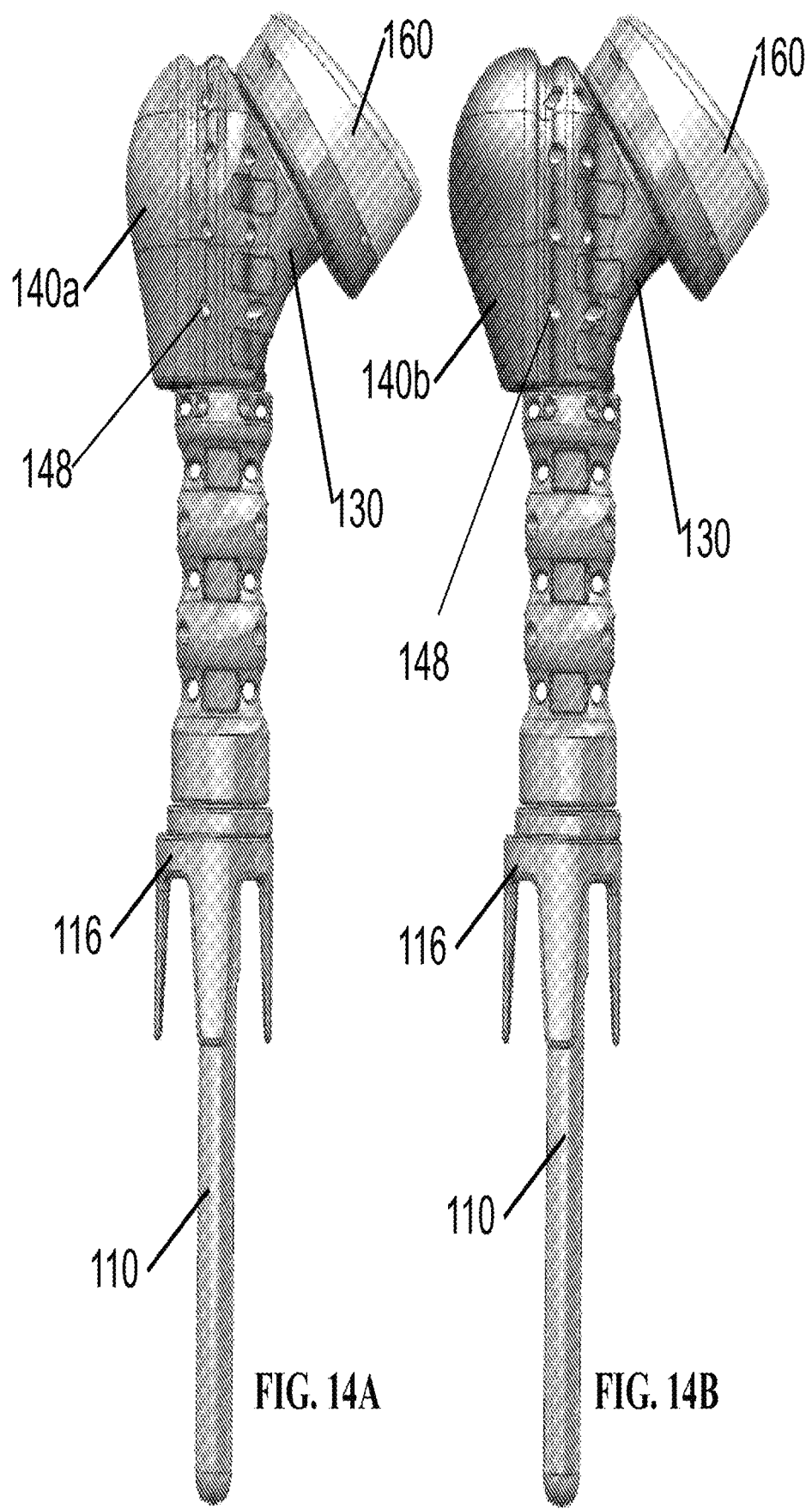

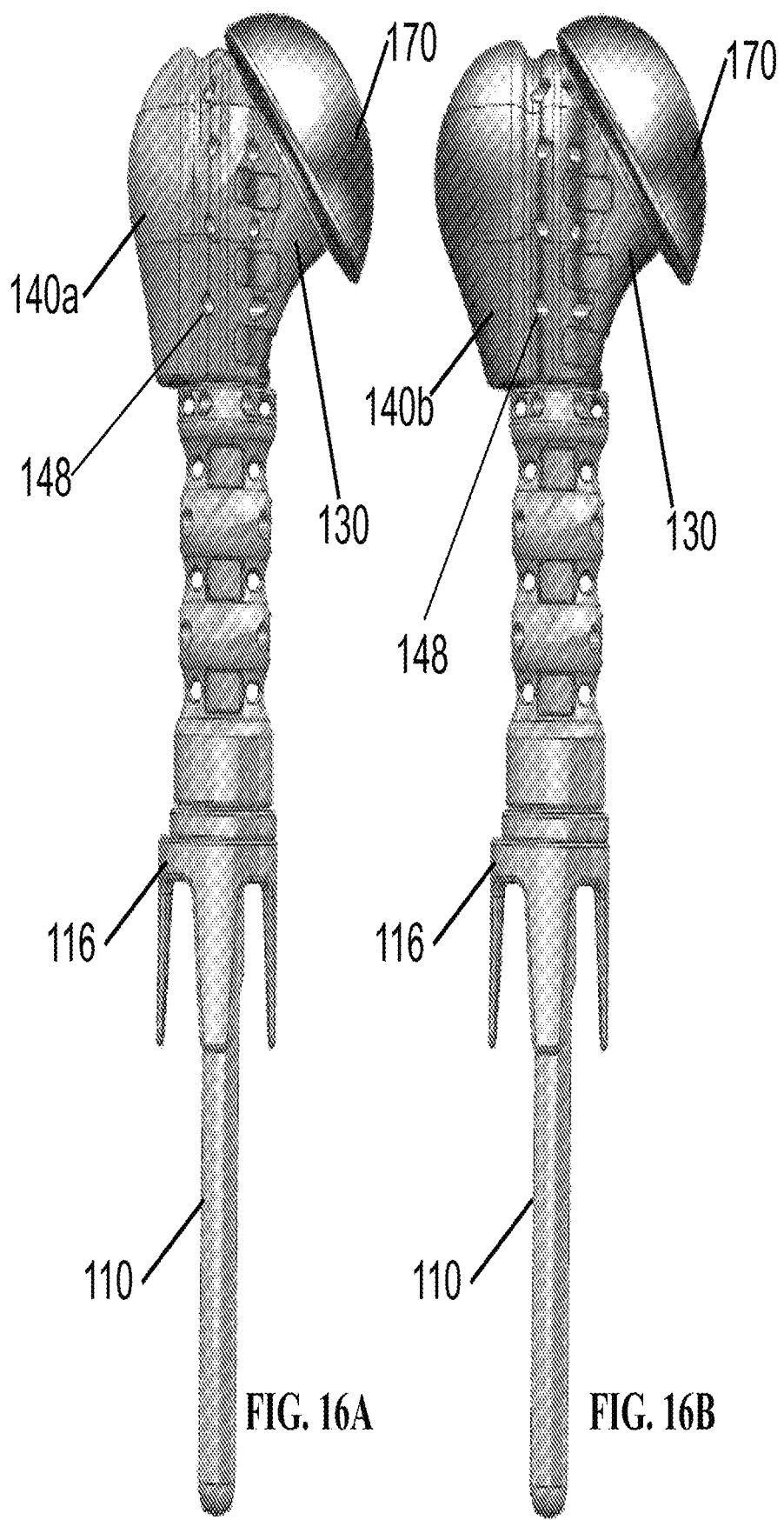

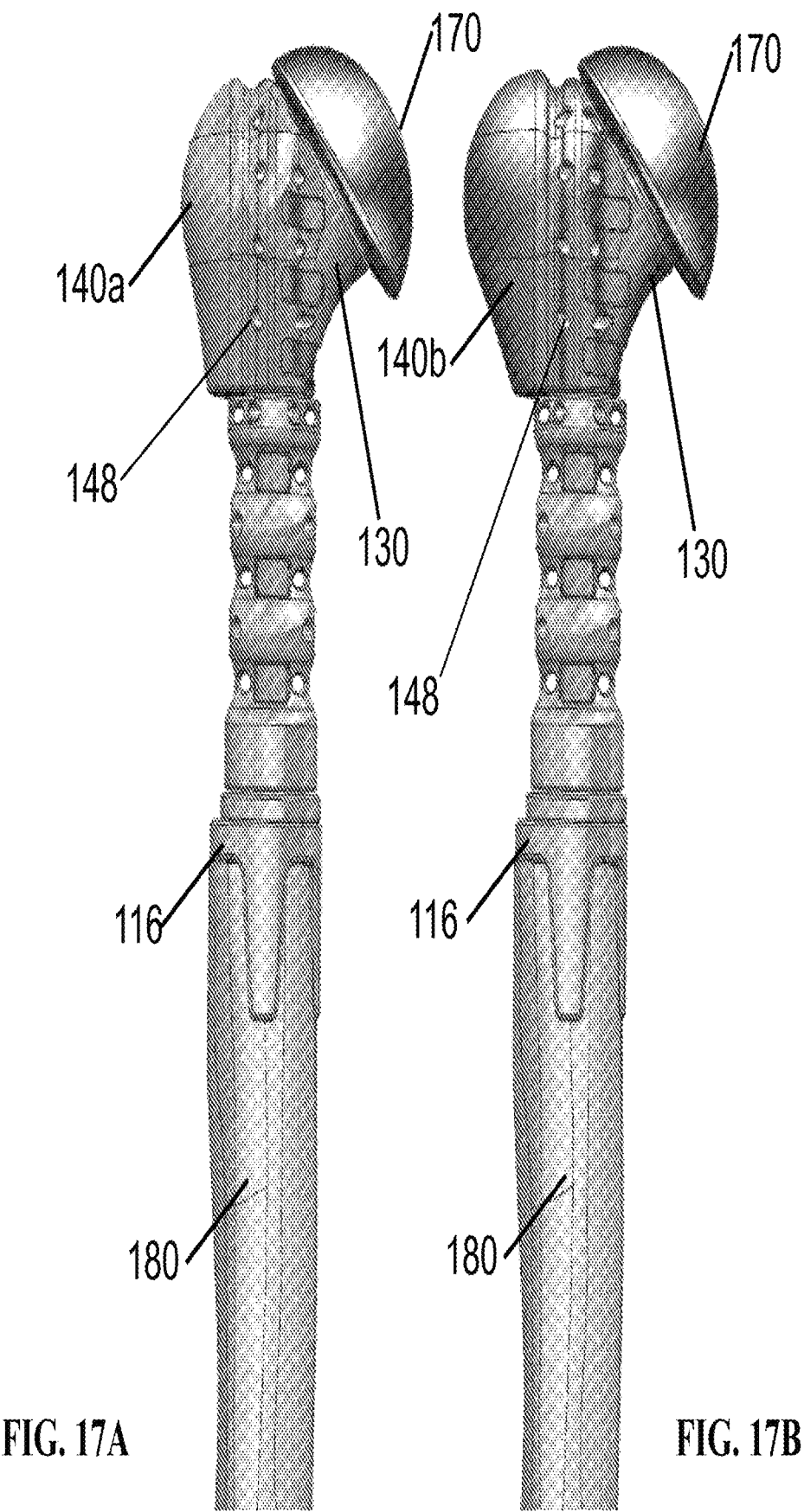

PROSTHETIC DEVICES TO IMPROVE JOINT MECHANICS IN ARTHROPLASTY

RELATED APPLICATIONS

This application is a continuation of U.S. patent application Ser. No. 13/955,083, filed Jul. 31, 2013, which claims the benefit of U.S. Provisional Application Ser. No. 61/678,353, filed Aug. 1, 2012 and U.S. Provisional Application Ser. No. 61/784,690, filed Mar. 14, 2013, and the entirety of these applications are hereby incorporated herein by reference for the teachings therein.

BACKGROUND

Muscles generate straight line forces that are converted to torques in proportion to their perpendicular distance between the joint center of rotation (CoR) and the muscle's line of action. This perpendicular distance is termed the muscle moment arm; thus, a 50% larger moment arm implies a 50% lower force required by a particular muscle to induce a given torque/motion. The location of the moment arm relative to the joint center of rotation determines the type of motion the muscle will create. In the shoulder, these motions are abduction/adduction (in the scapular/coronal plane and/or in the transverse plane), internal/external rotation (rotation of long axis of humerus), and flexion/extension (in the sagittal plane). The greater the muscle's moment arm, the greater capacity for that muscle to generate the torque required for motion and to support external loads. The trade off for a larger moment arm is that the muscle then requires a greater excursion (i.e. more muscle shortening to generate a given amount of motion). It should be recognized that a muscle's moment arm is only one component of a muscle's ability to generate torque, other factors include the muscle's physiologic cross sectional area, architecture, neural activity, and its length-tension relationship.

SUMMARY

Prosthetic devices to improve joint mechanics in arthroplasty are disclosed herein.

According to aspects illustrated herein, there are disclosed prosthetic devices which increase the tension of the deltoid and rotator cuff muscles by modifying their location of attachment and facilitating wrapping of the muscle around the device in such a manner that it can increase its moment arm, improve muscle tensioning, and facilitate greater joint compression to impart stability.

According to aspects illustrated herein, a prosthetic device of the present invention includes a humeral stem having a central longitudinal axis, the humeral stem configured to attach the prosthetic device to a resected bone; a proximal segment configured to directly or indirectly engage the humeral stem; and a tuberosity configured to engage the proximal segment, wherein the tuberosity is configured to have a thickness of at least 20 mm relative to the central longitudinal axis of the humeral stem so that the tuberosity is sufficiently positioned to simulate wrapping of a deltoid muscle to encourage joint compression. In an embodiment, the humeral stem is a modular humeral stem that allows full size interchangeability between component parts, yet provides superior resistance to component disengagement during use. In an embodiment, the prosthetic device further includes one or more middle segments engageably positionable between the proximal segment and the humeral stem. In an embodiment, a prosthetic device of the present invention is used during shoulder arthroplasty.

According to aspects illustrated herein, a kit of the present invention includes a humeral stem having a central longitudinal axis, the humeral stem configured to attach to a resected bone; a first tuberosity component having a first thickness relative to the central longitudinal axis of the humeral stem; a second tuberosity component having a second thickness relative to the central longitudinal axis of the humeral stem, wherein the first thickness of the first tuberosity component is different than the second thickness of the second tuberosity component; and at least one proximal segment configured to engage at least one of the first tuberosity component and the second tuberosity component. In an embodiment, the first thickness of the first tuberosity component is at least 20 mm relative to the central axis of the humeral stem, and the second thickness of the second tuberosity component is at least 20 mm relative to the central axis of the humeral stem.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIGS. 9A-9C show various embodiments (1 diameter, 3 lengths) of middle segments of a prosthetic device of the present invention.

FIG. 11A is a side view of the distal fixation ring and FIG. 11B is a bottom view of the distal fixation ring.

FIG. 12A is a side view of the assembly and FIG. 12B is a bottom view of the assembly.

FIG. 13A shows the prosthetic device of FIG. 6 with a "standard" size tuberosity, FIG. 13B shows the prosthetic device of FIG. 6 with a "first expanded" size tuberosity, and FIG. 13C shows the prosthetic device of FIG. 6 with a "second expanded" size tuberosity.

FIGS. 14A and 14B are side views of an embodiment of a prosthetic device of the present invention for use with a reverse shoulder. The device includes a humeral stem, a middle segment, and a proximal segment with a standard size tuberosity (FIG. 14A) and an expanded size tuberosity (FIG. 14B).

FIGS. 16A and 16B are side views of an embodiment of a prosthetic device of the present invention for use with an anatomic total shoulder. The device includes a humeral stem, a middle segment, and a proximal segment with a standard size tuberosity (FIG. 16A) and an expanded size tuberosity (FIG. 16B).

FIGS. 17A and 17B are side views of the prosthetic devices of FIGS. 16A and 16B when assembled to a humeral bone. In these images, the distal fixation ring fits around the diaphysysis of the humeral bone; the stem and ring are each provided in various sizes and are each offset to permit a better fit in each size humerus.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments. Those skilled in the art will recognize that a prosthetic device of the present invention has applications in joints including, but not limited to, the shoulder, the hip and the knee.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components (and any size, material and similar details shown in the figures are, of course, intended to be illustrative and not restrictive). Therefore, specific structural and functional details disclosed herein are not to be interpreted as limiting, but merely as a representative basis for teaching one skilled in the art to variously employ the present invention.

Reduced muscle function with arthroplasty is a complicated issue. In the shoulder, prosthetic design parameters can alter the tension of the muscles above or below their normal resting length and or strategically increase (or decrease) the moment arms of muscles to make them more (or less) important contributor to a given type of motion. In the shoulder, with reverse shoulder arthroplasty, two of the most common muscle-related challenges are instability and loss of external rotation (and excessive internal rotation), the later of which impairs the patient's ability to maintain their arm in neutral rotation as the arm is elevated (e.g. positive horn blower's sign), preventing numerous activities of daily living. These issues are particularly worrisome in oncology or revision applications in which the bone is removed and the soft tissue is required to be reconstructed to a different substrate which may or may not occur at a different point in space.

Figure 1:
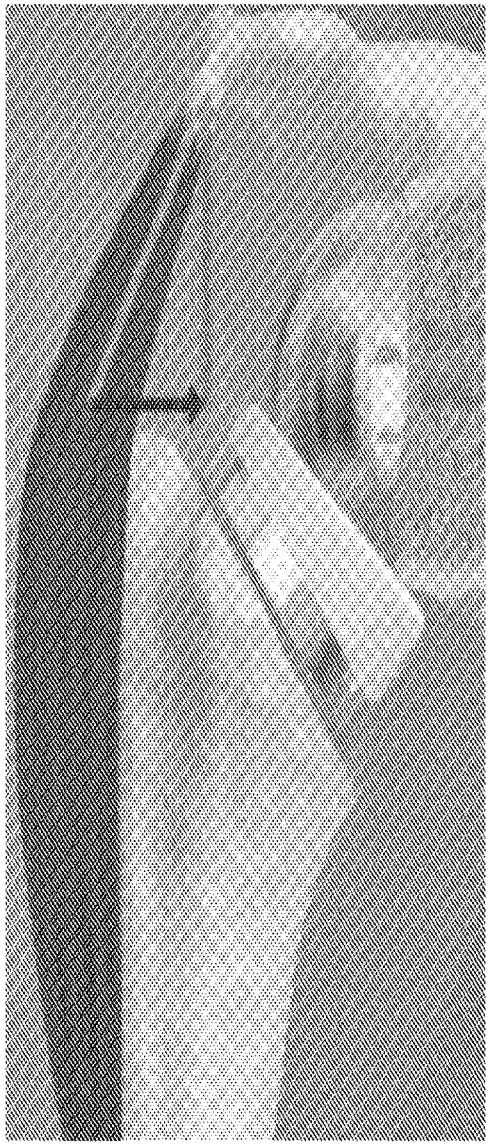
FIG. 1 is a photograph showing the middle deltoid muscle wrapping around the greater tuberosity of the humeral head to increase the stability via humeral head compression.

The deltoid is the largest and most important muscle in the shoulder girdle. It is the primary mover in the shoulder, and generates forward elevation in the scapular plane. The deltoid consists of three distinct heads: 1) anterior (anterior acromion and clavicle), 2) middle (lateral margin of the acromion), and 3) the posterior deltoid (scapular spine); and accounts for approximately 20% of the mass of the shoulder muscles. At low levels of abduction, the wrapping of the middle deltoid muscle around the greater tuberosity of the humeral head (FIG. 1) generates a stabilizing compressive force; however, this compressive force is small relative to that generated by the rotator cuff.

Changing the joint center of rotation with arthroplasty (specifically, with a reverse shoulder in which the inversion of the anatomic concavities and the inferior and medial shift of the center of rotation) dramatically alters the relationship of each (shoulder) muscle to its normal physiologic function. In the shoulder, medially shifting the center of rotation increases the length of the anterior, middle, and posterior deltoid abduction moment arms and lengthens the anterior, middle, and posterior deltoid allowing them to contribute more toward abduction. These larger abductor moment arms enhance the capacity of the deltoid to elevate the arm in the scapular and coronal planes, compensating for the impaired function of the supraspinatus and the superior portions of the subscapularis and infraspinatus rotator cuff muscles which are typically involved in the indicated pathology. Medially shifting the center of rotation also translates the humerus medially which increases the laxity of any remaining rotator cuff muscles and also leads to impingement of the humerus with the scapular neck at low elevation (i.e. scapular notching).

Restoring the lateral position of the humeral tuberosities is important to tension the remaining rotator cuff muscles in a more natural physiologic manner and offers the potential to better restore rotational strength. While over-tensioning these muscles may offer the possibility of improved resting tone/tension, it may also make it more difficult to repair following tenotomy (in the case of the subscapularis).

Figure 2:
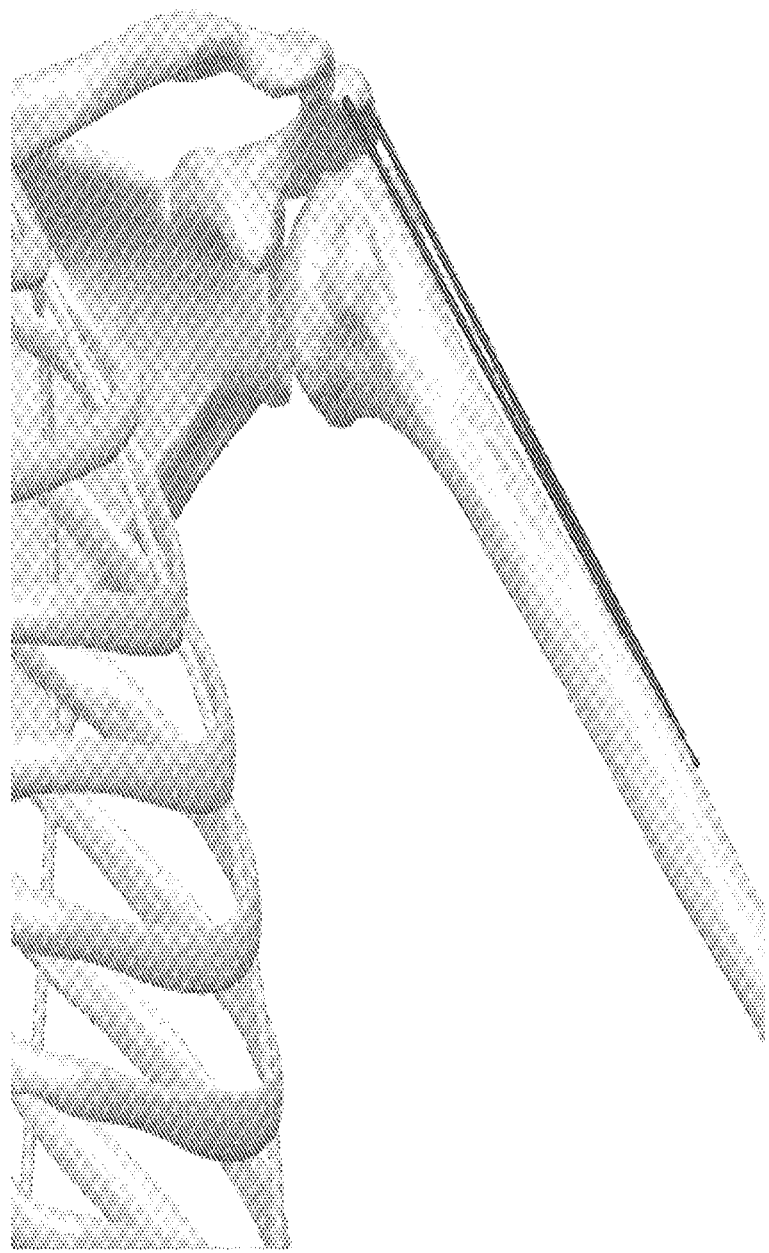
FIG. 2 is a computer model of the normal shoulder abducted to 48 degrees relative to a fixed scapula in which the middle deltoid muscle no longer wraps the greater tuberosity of the humeral head and therefore no longer imparts a stabilizing compressive force to the glenoid.
Figure 3:
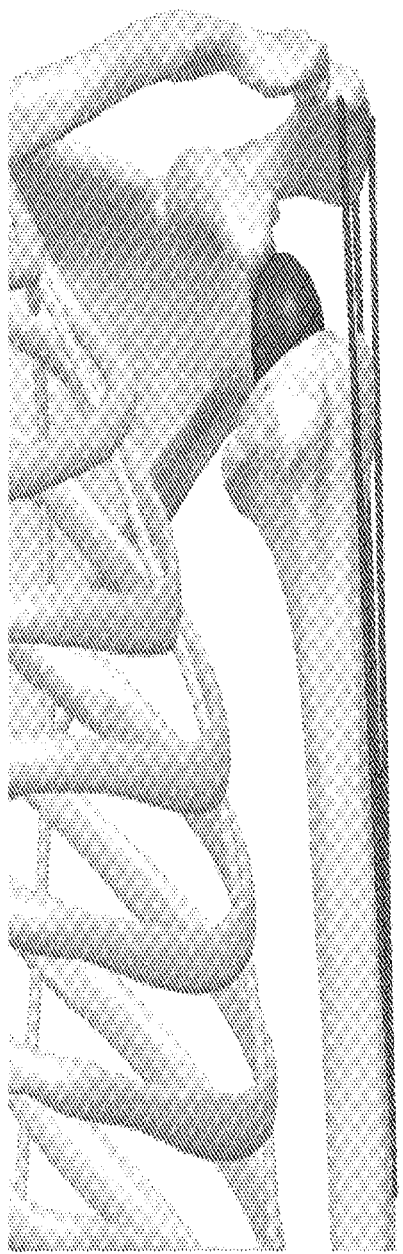
FIG. 3 is a computer model of a 36 mm Grammont reverse shoulder abducted to 8 degrees relative to a fixed scapula in which the middle deltoid muscle no longer wraps the greater tuberosity of the humeral head and therefore no longer imparts a stabilizing compressive force to the glenoid.
Figure 4:
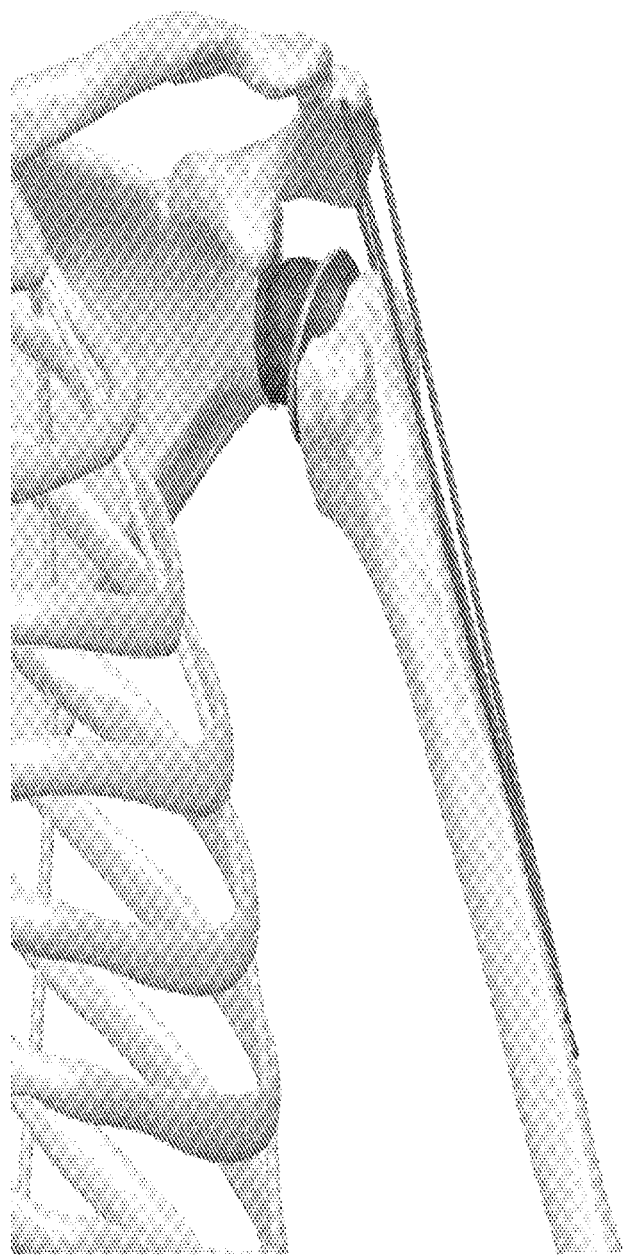
FIG. 4 is a computer model of a 32 mm Encore Reverse® shoulder abducted to 28 degrees relative to a fixed scapula in which the middle deltoid muscle no longer wraps the greater tuberosity of the humeral head and therefore no longer imparts a stabilizing compressive force to the glenoid.
Figure 5:
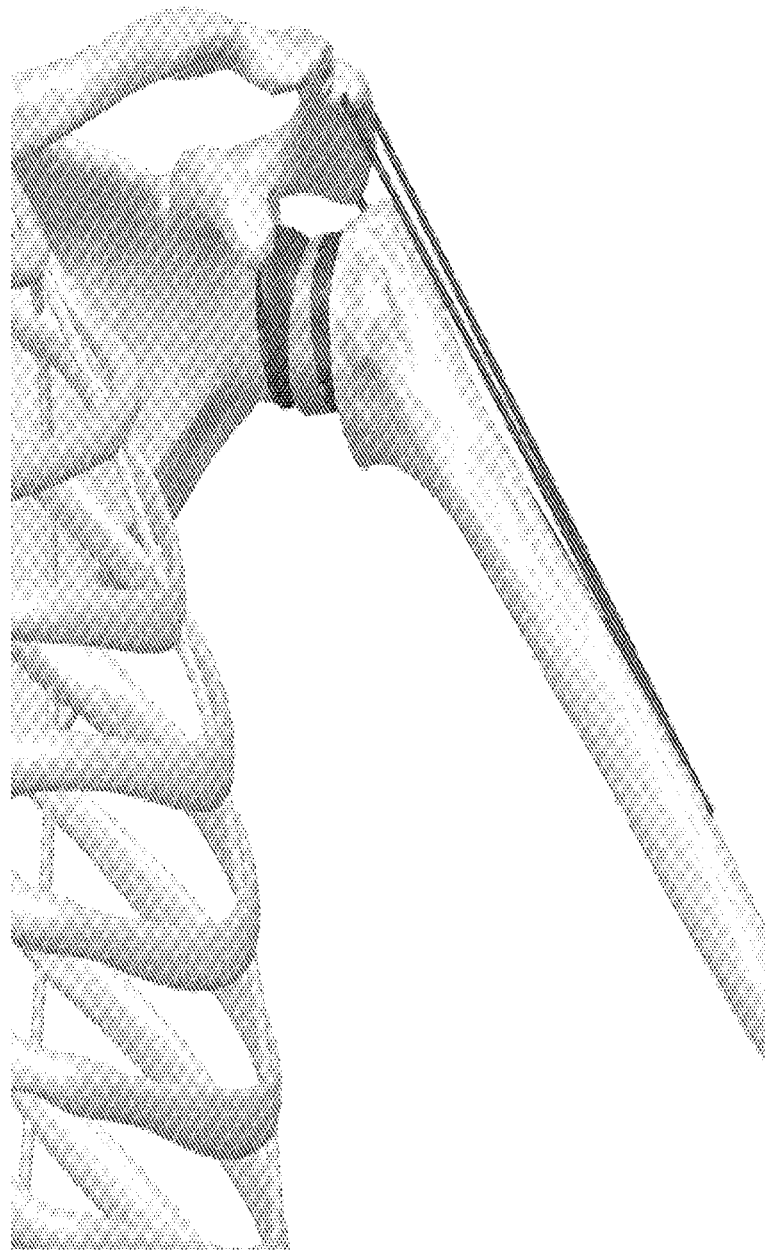
FIG. 5 is a computer model of a 38 mm Equinoxe® reverse shoulder abducted to 40 degrees relative to a fixed scapula in which the middle deltoid muscle no longer wraps the greater tuberosity of the humeral head and therefore no longer imparts a stabilizing compressive force to the glenoid.

Lateralizing the joint center of rotation relative to the Grammont design has been proposed as a method to improve active internal and external rotation, strength, and stability. Lateralizing the joint center of rotation lateralizes the humerus, tensions the remaining rotator cuff muscles, and minimizes impingement of the humeral component along the inferior scapular neck. Lateralizing the joint center of rotation also increases the torque on the glenoid fixation surface and decreases the lengths of the deltoid abductor moment arms. Because the deltoid abductor moment arms are decreased as the center of rotation is lateralized, the deltoid becomes less effective as an abductor and requires a greater force to elevate the arm in both the scapular and coronal planes. These elevated loads and torques can have negative implications on patient rehab, muscle fatigue, stress fractures, and prosthesis fixation. It should be recognized that the humerus can be lateralized without lateralizing the joint center of rotation. Doing so, has the advantage of restoring the anatomic rotator cuff muscle length/tension while maintaining Grammont's abductor moment arm lengths and minimizing the torque on the glenoid-bone interface. Roche et al. first demonstrated that the humerus can be lateralized to place the tuberosities in a more anatomic position while minimizing humeral liner impingement with the inferior scapular neck. This can be accomplished by decreasing the humeral neck angle from the Grammont humeral neck angle of 155°, proportionally increasing the Grammont glenosphere diameter and thickness, decreasing the humeral liner constraint, and/or by increasing the medial offset of the humeral liner/humeral stem. Lemieux et al. demonstrated that increasing the medial offset of the humeral stem in total shoulder arthroplasty increased the middle deltoid moment arm and also increased the middle deltoid wrapping angle about the greater tuberosity which helps to stabilize the joint by compressing the humeral head into the glenoid fossa. As described in Table 1, deltoid wrapping can be altered by different prosthesis designs (Grammont reverse shoulder, Encore reverse shoulder, vs Equinoxe reverse shoulder), different orientations (e.g. changing humeral retroversion and or changing the tilt of the implant), and/or implanting the device in a scapula with varying scapular morphology or wear patterns (e.g. medial glenoid wear). These results were calculated from a computer model which simulates muscle lines of action in the shoulder during various arm positions. FIG. 2 is a computer model illustrating the arm abduction in which the middle deltoid muscle ceases to wrap the humeral head greater tuberosity in the normal shoulder at 48° abduction in the scapular plane (relative to a fixed scapula). FIGS. 3-5 are computer models illustrating the same deltoid wrapping phenomenon with varying reverse shoulder prosthesis designs (36 mm Grammont reverse shoulder abducted to 8° relative to a fixed scapula (FIG. 3), 32 mm Encore Reverse® shoulder abducted to 28° relative to a fixed scapula (FIG. 4), and 38 mm Equinoxe® reverse shoulder abducted to 40° relative to a fixed scapula (FIG. 5). In FIGS. 3-5 the middle deltoid muscle no longer wraps the greater tuberosity of the humeral head and therefore no longer imparts a stabilizing compressive force to the glenoid.

TABLE 1

Wrapping of Middle Deltoid Around Greater Tuberosity (computer modeling study)

| | Abduction where deltoid doesn't wrap tuberosity |
|---|---|
| Normal Shoulder | 48° |
| 36 Grammont, 20° retroversion | 8° |
| 32 Encore Reverse ® | 28° |
| 38 Equinoxe ® | 40° |
| 36 Grammont, 0° retroversion | 16° |
| 36 Grammont, 40° retroversion | 7° |
| 36 Grammont, 15° tilt | 7° |
| 32 Encore Reverse ®, 15° tilt | 21° |
| 36 Grammont, 10 mm medial wear | −1° |
| 32 Encore Reverse ®, 10 mm medial wear | 12° |
| 38 Equinoxe ®, 10 mm medial wear | 18° |

Figure 6:
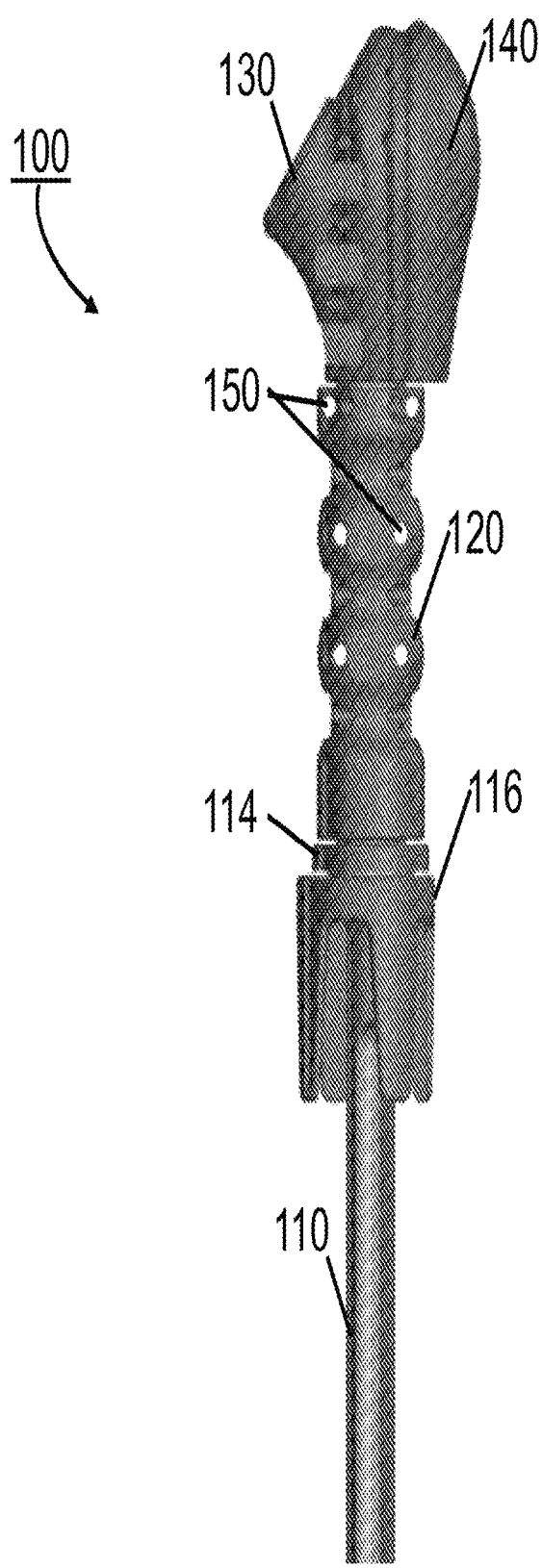
FIG. 6 shows a side view of an embodiment of a prosthetic device of the present invention which can be used for either anatomic or reverse total shoulder arthroplasty. The device includes a humeral stem, a middle segment, a proximal segment and a tuberosity. In this embodiment, the humeral stem includes an offset taper for connecting to a distal fixation ring.

FIG. 6 shows a side view of an embodiment of a prosthetic device 100 of the present invention which can be used for either anatomic or reverse total shoulder arthroplasty, and can also be used for hip arthroplasty. The device 100 includes a humeral stem 110, a middle segment 120, a proximal segment 130, and a tuberosity 140. In an embodiment, the humeral stem 110 includes an offset taper 114 for connecting to a distal fixation ring 116. The proximal segment 130 lateralizes the location where the soft tissue in the shoulder inserts to the device 100 (specifically, the rotator cuff—attached with suture holes) and also lateralizes where the deltoid muscle wraps around the device 100 to facilitate the wrapping angle to impart greater compression into the glenoid. In an embodiment, the device 100 does not include a middle segment 120. In an embodiment, the device 100 includes two or more middle segments 120. The device 100 may include multiple suture bores 150 for soft tissue fixation.

Figures 7A, 7B, 7C:
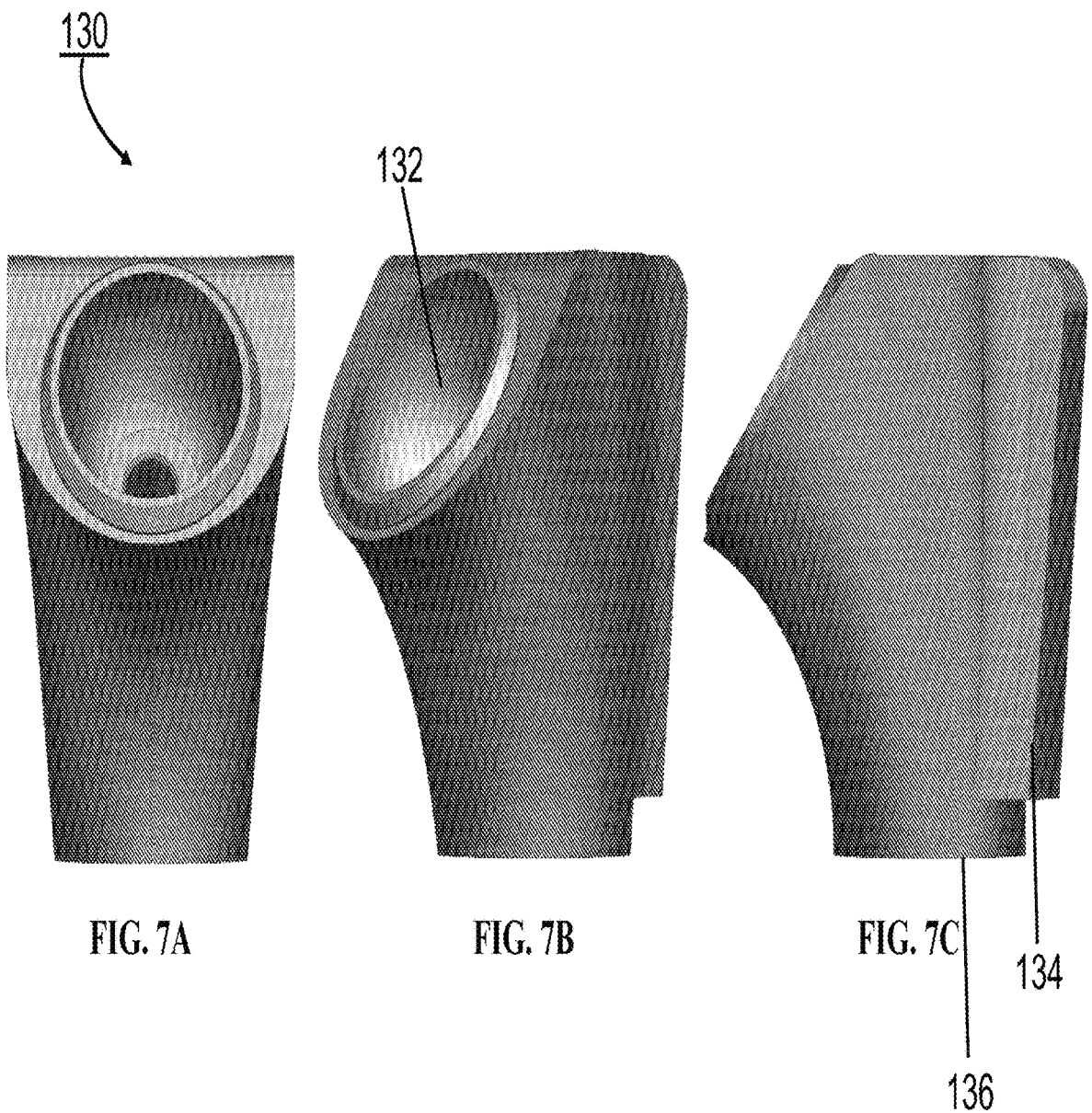
FIGS. 7A-7C show various views of an embodiment of a proximal segment of a prosthetic device of the present invention.

FIGS. 7A-7C show various views of the proximal segment 130. In an embodiment, the proximal segment 130 is manufactured from Ti-6Al-4V. In an embodiment, the proximal segment 130 is solution heat and thermal aged. In an embodiment, the proximal segment 130 is +0 mm in length. In an embodiment, the proximal segment 130 is +12.5 mm in length. In an embodiment, the proximal segment 130 includes a spherical bore 132 for attachment to a humeral tray of a reverse shoulder prosthesis (see, for example, FIGS. 14A and 14B) or for attachment to a replicator plate of a primary shoulder prosthesis (see, for example, FIGS. 16A and 16B). In an embodiment, the proximal segment 130 includes a tapered portion 134 for attachment with various sizes of modular tuberosity components of the present invention. In an embodiment, the proximal segment 130 includes a connection 136 which is configured to lockingly engage a connection 122 of a middle segment 120 of the present invention or lockingly engage a connection 112 of the humeral stem 110 of the present invention.

Figure 8A:
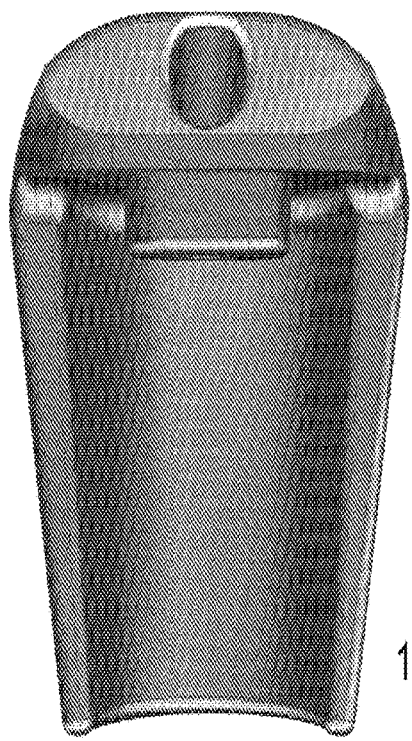
FIGS. 8A-8C show various views of an embodiment of a tuberosity of a prosthetic device of the present invention.
Figure 8B:
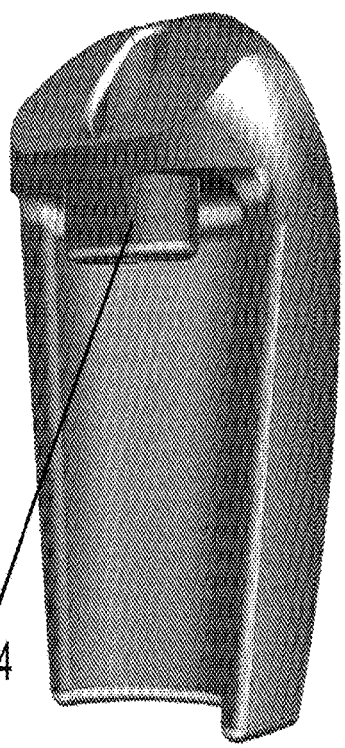
Figure 8C:
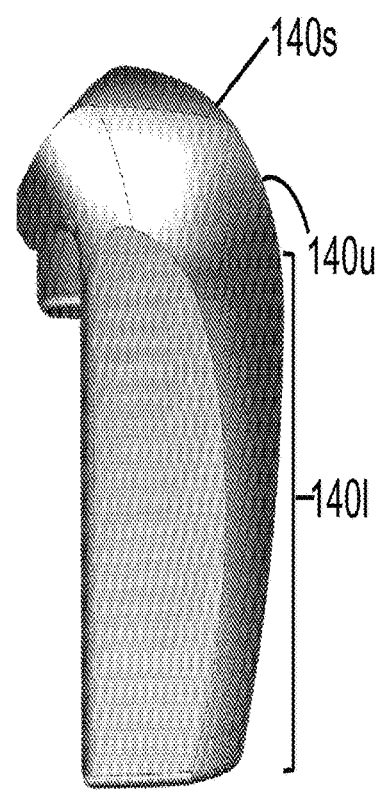

FIGS. 8A-8C show various views of an embodiment of a tuberosity 140 of the present invention. In an embodiment, the tuberosity 140 is manufactured from Ti-6Al-4V. In an embodiment, the tuberosity 140 is manufactured from Co—Cr. In an embodiment, an outer surface 140s of the tuberosity 140 is smooth (electro-polished) to prevent abrasion or damage to the deltoid muscle as it slides over the outer surface 140s of the tuberosity 140. The outer surface 140s of the tuberosity includes a lower portion 1401 that is substantially a flat surface and an upper portion 140u with a convex curvature configured so as to allow the deltoid muscle to wrap around a greater tuberosity of a humeral head. In an embodiment, the tuberosity 140 includes a mating connection 144 for attachment with a proximal segment 130 of the present invention.

FIGS. 9A-9C show various embodiments (1 diameter, 3 lengths) of middle segments 120 of the device 100 of the present invention. In an embodiment, each middle segment 120 has the same diameter, for example, 24 mm with suture cage 126. In an embodiment, the middle segment 120 has a length of 25 mm (FIG. 9A). In an embodiment, the middle segment 120 has a length of 50 mm (FIG. 9B). In an embodiment, the middle segment 120 has a length of 75 mm (FIG. 9C). The middle segments 120 include an axial bore therethrough. In an embodiment, the axial bore of the middle segment 120 includes a first tapered portion 122 and a second tapered portion 124, the first tapered portion 122 located adjacent a proximal end of the middle segment 120 and dimensionally configured to lockingly engage the tapered portion 136 of the proximal segment 130, the second tapered portion 124 located adjacent a distal end of the middle segment 120 and dimensionally configured to lockingly engage the tapered portion 112 of the humeral stem 110. Each of the segments 120 may be constructed from a biocompatible, high strength titanium alloy, but may also be constructed from other biocompatible materials such as cobalt chrome alloy, stainless steel, and composite materials. In an embodiment, the middle segment 120 is manufactured from Ti-6Al-4V. A threaded screw may optionally be used to enhance locking engagement of the segments. In an embodiment, the middle segment 120 is solution heat treated and thermal aged. The middle segments 120 may be coated with a soft tissue fixation material such as plasma coating.

Figure 10:
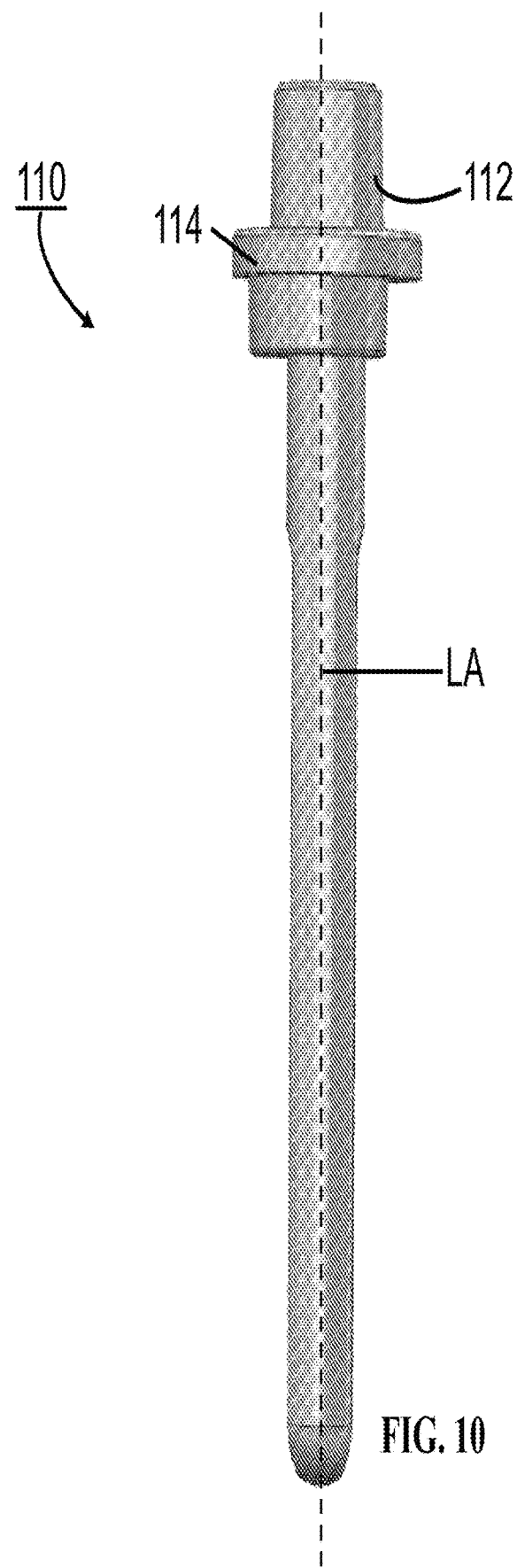
FIG. 10 shows an embodiment of a humeral stem of a prosthetic device of the present invention with an offset taper for connecting to a distal fixation ring of the present invention.

FIG. 10 shows an embodiment of the humeral stem 110 of the device 100 of the present invention with an offset taper 114 for connecting to the distal fixation ring 116 of the present invention. In an embodiment, the taper 114 is offset from the central longitudinal axis "LA" of the humeral stem 110 by about 1 mm. The humeral stem 110 may be offset to facilitate a better fit between the outer humeral diaphsysis and the inner intramedullary diameter. In an embodiment, the humeral stem 110 is available in three different lengths, and six different diameters, yielding eleven stems 110 (6×80/120, 7×80/120, 8×80/120/200, 9×80/120, 11×120, 13×120).

Figure 11A:
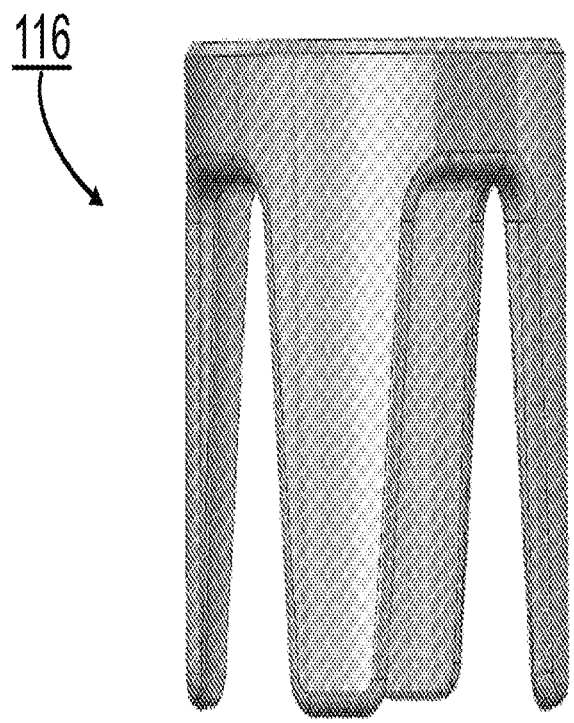
FIGS. 11A and 11B show an embodiment of a distal fixation ring of a prosthetic device of the present invention with an offset taper for connecting to the humeral stem.
Figure 11B:
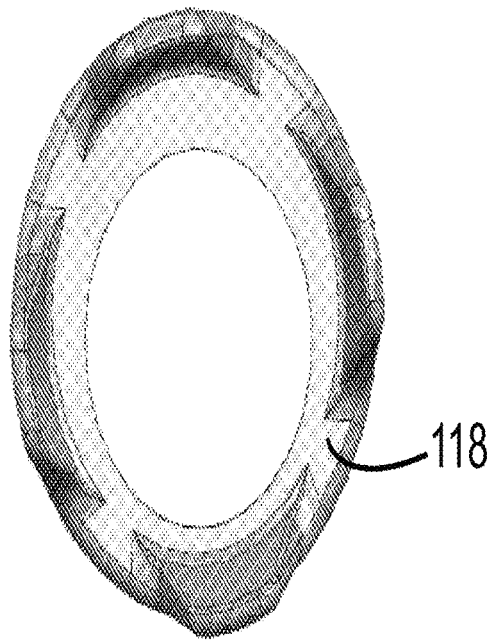

FIGS. 11A and 11B show the distal fixation ring 116 of the device 100 with an offset taper (offset from the central longitudinal axis of the ring 116) for connecting to the humeral stem. In an embodiment, the central longitudinal axis of the ring 116 is offset by about 1 mm. Distal fixation ring 116 has an under surface 118 which abuts cancellous bone forming the face of the resected bone (as visible in FIGS. 15A, 15B, 17A, 17B and 19B-I). The dimensions of the distal fixation ring 116 are selected so that the end face of ring 116 approximates to the dimensions of the resected end face of the resected bone. In an embodiment, the ring 116 may be coated with a soft tissue fixation material such as plasma coating and may be coated with a bone growth stimulating material such as hydroxyapatite, which can encourage cancellous bone to grow over the surface of the ring 116 and help to more firmly lock the device 100 into the residual resected bone.

Figures 12A, 12B:
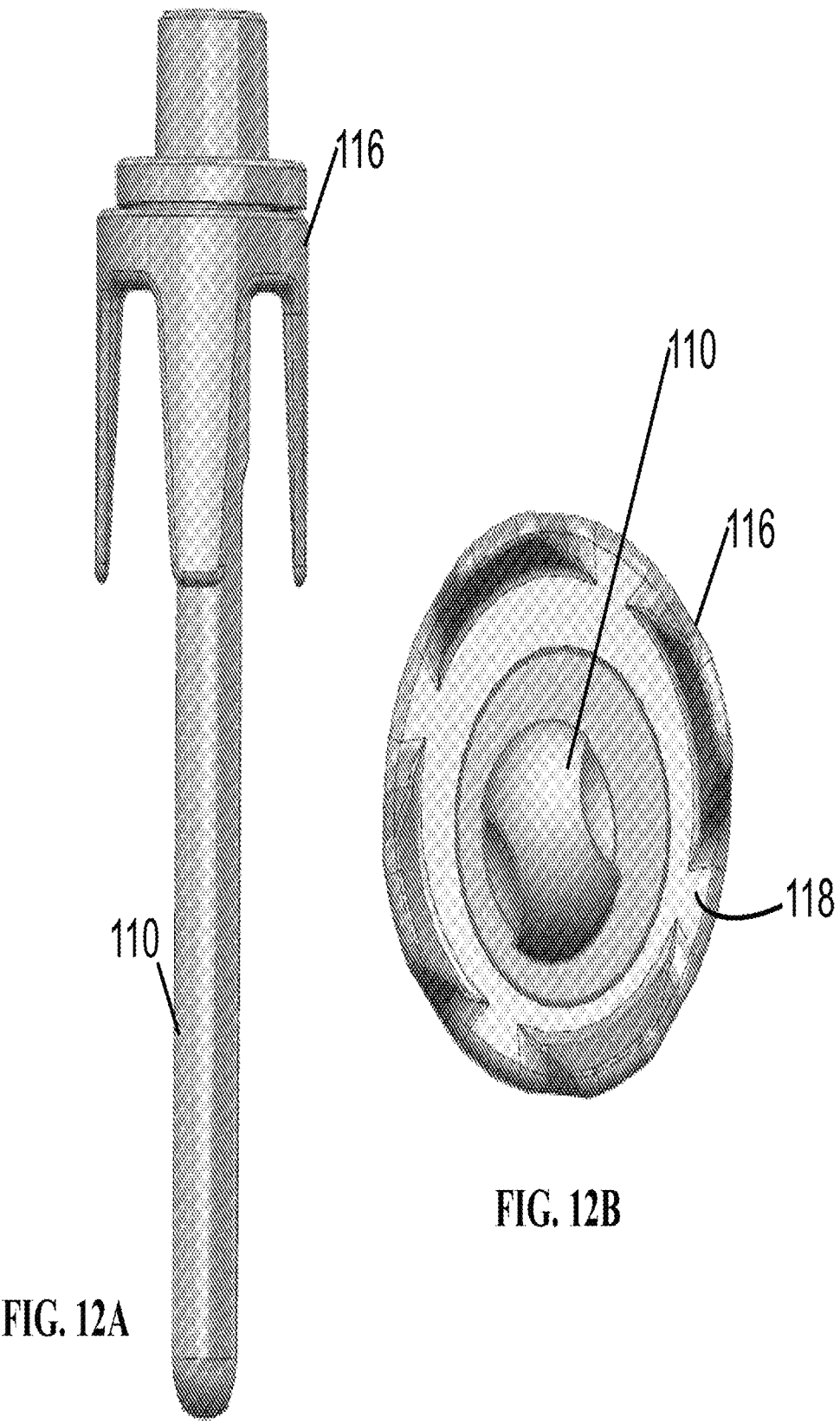
FIGS. 12A and 12B show the assembly of the distal fixation ring with an offset taper and the humeral stem with an offset taper.

FIGS. 12A and 12B shows the humeral stem of FIG. 10 and the distal fixation ring 116 of FIG. 11A in which each has an offset to decouple the offset of the outer humeral diaphysis diameter from any offset in the inner intramedullary canal diameter.

Figures 13A, 13B, 13C:
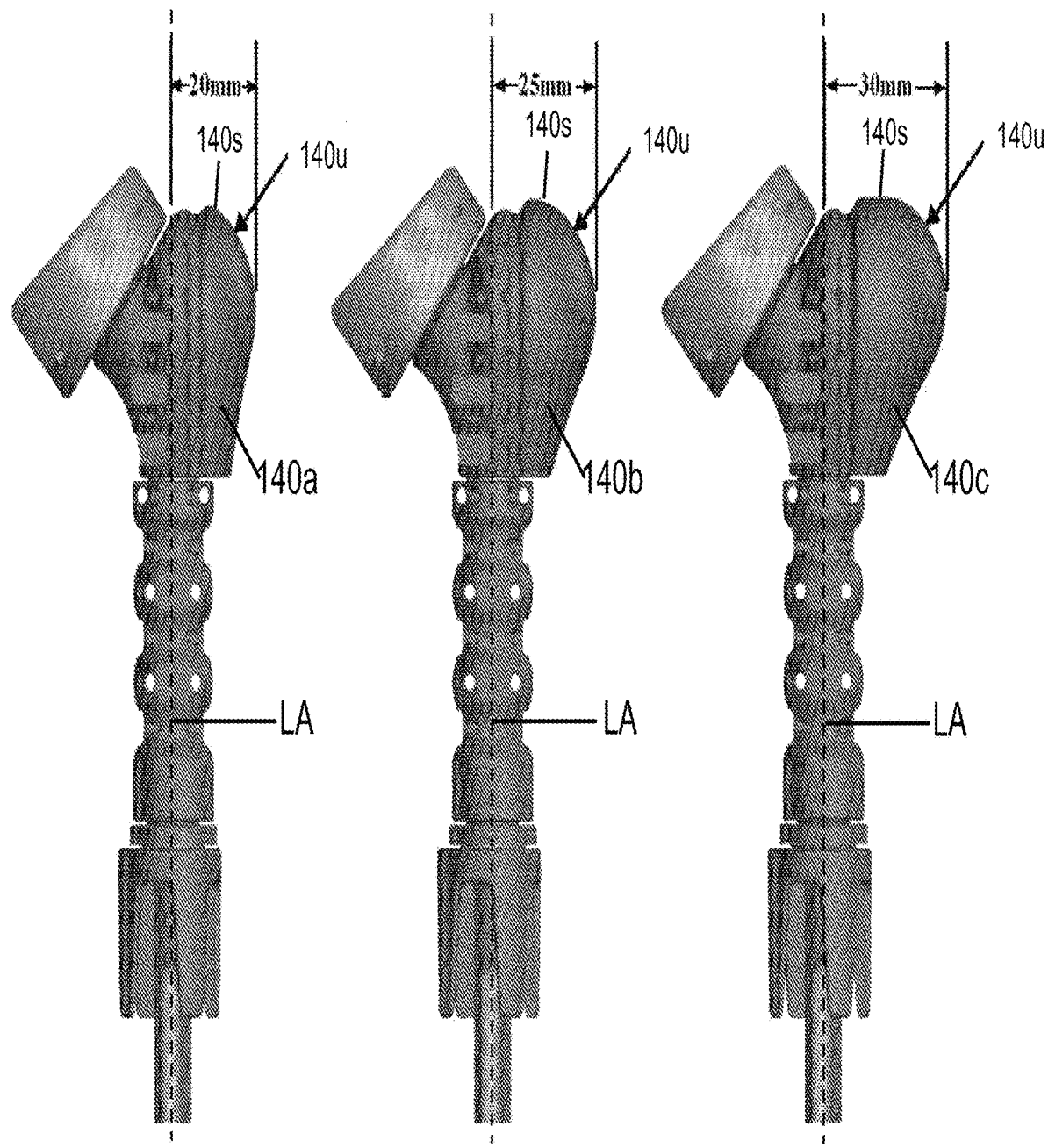
FIGS. 13A-13C show three embodiments of tuberosities of the present invention.

FIGS. 13A-13C show three embodiments of tuberosities of the present invention. FIG. 13A shows a first tuberosity 140a of the present invention having a first thickness of 20 mm measured from the central longitudinal axis "LA" of the humeral stem 110 to the outer surface 140s and is considered a "standard" size (+0 mm) tuberosity 140a of the present invention. FIG. 13B shows a second tuberosity 140b of the present invention having a second thickness of 25 mm measured from the central longitudinal axis "LA" of the humeral stem 110 to the outer surface 140s and is considered a "first expanded" size (+5 mm) tuberosity 140b of the present invention. FIG. 13C shows a third tuberosity 140c of the present invention having a third thickness of 30 mm measured from the central longitudinal axis "LA" of the humeral stem 110 to the outer surface 140s and is considered a "second expanded" size (+10 mm) tuberosity 140c of the present invention. The different tuberosities allow intraoperative modification of deltoid muscle wrapping. In an embodiment, each tuberosity includes a mating connection 144 for attachment to the proximal segment 130 of the present invention. In an embodiment, the tuberosity 140a is sufficiently designed to have a thickness of 20 mm relative to the central longitudinal axis "LA" of the humeral stem 110 so that the tuberosity is sufficiently positioned to simulate wrapping of the deltoid to encourage joint compression. The lateral margin of the tuberosity features is defined as the distance of 20 mm but may be increased to selectively facilitate more deltoid wrapping and greater joint compression. For example, tuberosity components 140b and 140c are provided with a thickness of 25 mm (+5 mm) and 30 mm (+10 mm), respectively, relative to the central longitudinal axis "LA" of the humeral stem 110 in order to selectively facilitate more deltoid muscle wrapping and greater joint compression. Tuberosities 140a, 140b, and 140c include outer surfaces 140s having an upper portion 140u with a convex rounded curvature. In an embodiment, the upper portion 140u with the convex rounded curvature of each tuberosity 140a, 140b, and 140c has a radius of curvature that is substantially the same. In an embodiment, the upper portion 140u with the convex rounded curvature of tuberosity 140a has a radius of curvature of 16.5 mm. In an embodiment, the upper portion 140u with the convex rounded curvature of tuberosity 140b has a radius of curvature of 16.0 mm. In an embodiment, the upper portion 140u with the convex rounded curvature of tuberosity 140c has a radius of curvature of 15.0 mm.

FIGS. 14A and 14B are side views of prosthetic device 100 used with components of a reverse shoulder. In FIG. 14A, the "standard" size tuberosity 140a is illustrated, while in FIG. 14B, the "first expanded" size tuberosity 140b is illustrated. In an embodiment, the tuberosity 140a, 140b, is modularly connected to the proximal segment 130. The tuberosity may include embedded suture holes 148 at various locations to selectively tension/reattach rotator cuff muscles. In an embodiment, the humeral stem 110 is a modular humeral stem. As illustrated in FIGS. 14A and 14B, the device 100 includes a humeral liner 160. A tuberosity 140 of the present invention can be integral to the proximal segment 130 or modularly engage the proximal segment 130.

Figures 15A, 15B:
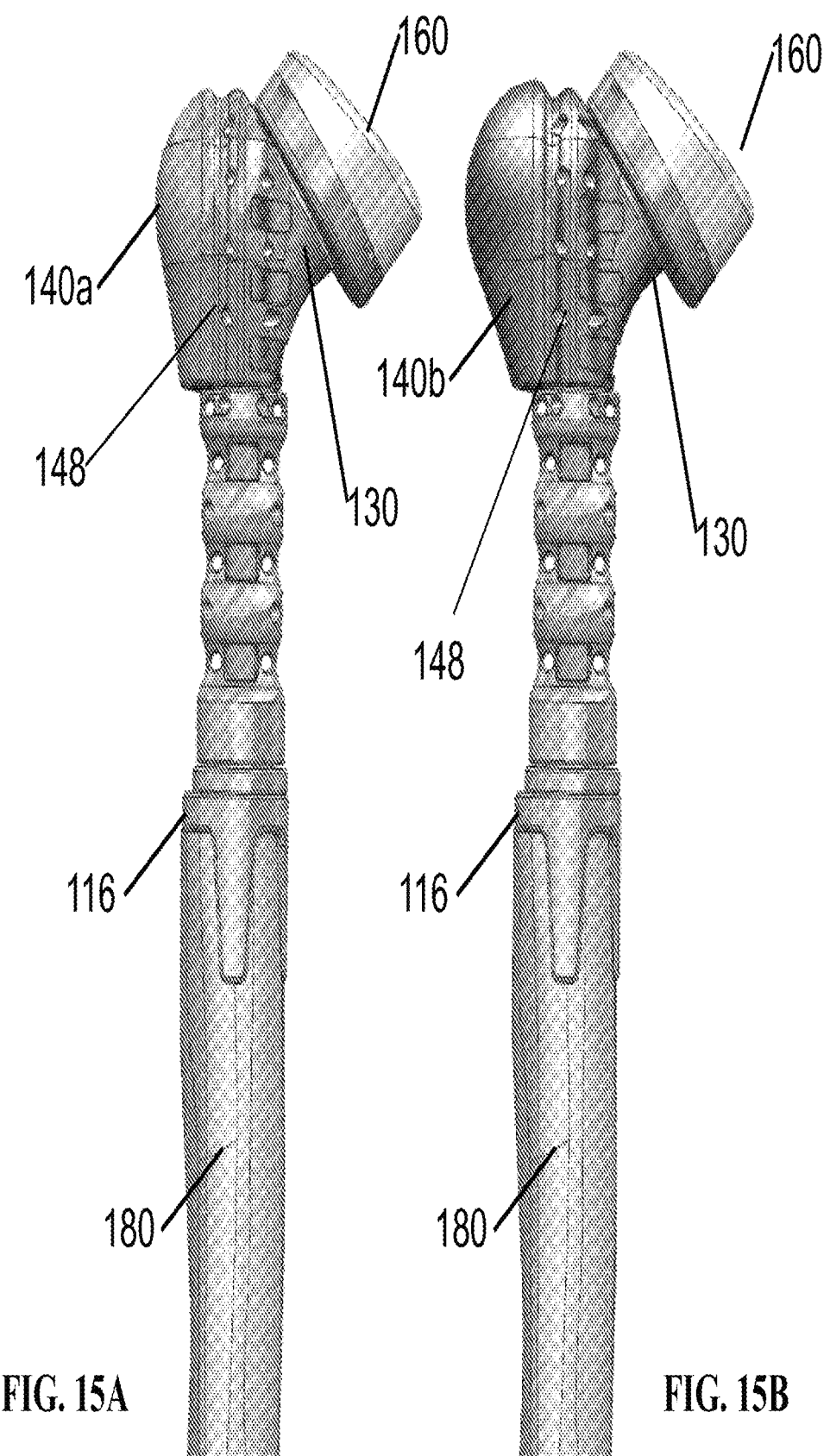
FIGS. 15A and 15B are side views of the prosthetic devices of FIGS. 14A and 14B when assembled to a humeral bone. In these images, the distal fixation ring fits around the diaphysysis of the humeral bone; the stem and ring are each provided in various sizes and are each offset to permit a better fit in each size humerus.

FIGS. 15A and 15B are side views of the prosthetic devices of FIGS. 14A and 14B when assembled to a humeral bone. In these images, the distal fixation ring 116 fits around the diaphsysis of the humeral bone 180; the stem 110 and ring 116 are each provided in various sizes and are each offset to permit a better fit in each size humerus.

FIGS. 16A and 16B are side views of prosthetic device 100 used with components of an anatomic total shoulder. In FIG. 16A, the "standard" size tuberosity 140a is illustrated, while in FIG. 16B, the "first expanded" size tuberosity 140b is illustrated. In an embodiment, the tuberosity 140*a*, 140*b*, is modularly connected to the proximal segment 130. The tuberosity may include embedded suture holes 148 at various locations to selectively tension/reattach rotator cuff muscles. In an embodiment, the humeral stem 110 is a modular humeral stem. As illustrated in FIGS. 16A and 16B, the device 100 includes a replicator plate (not visible) and a humeral head 170. A tuberosity 140 of the present invention can be integral to the proximal segment 130 or modularly engage the proximal segment 130.

FIGS. 17A and 17B are side views of the prosthetic devices of FIGS. 16A and 16B when assembled to a humeral bone. In these images, the distal fixation ring 116 fits around the diaphsysis of the humeral bone 180; the stem 110 and ring 116 are each provided in various sizes and are each offset to permit a better fit in each size humerus.

Figures 18A, 18B, 18C:
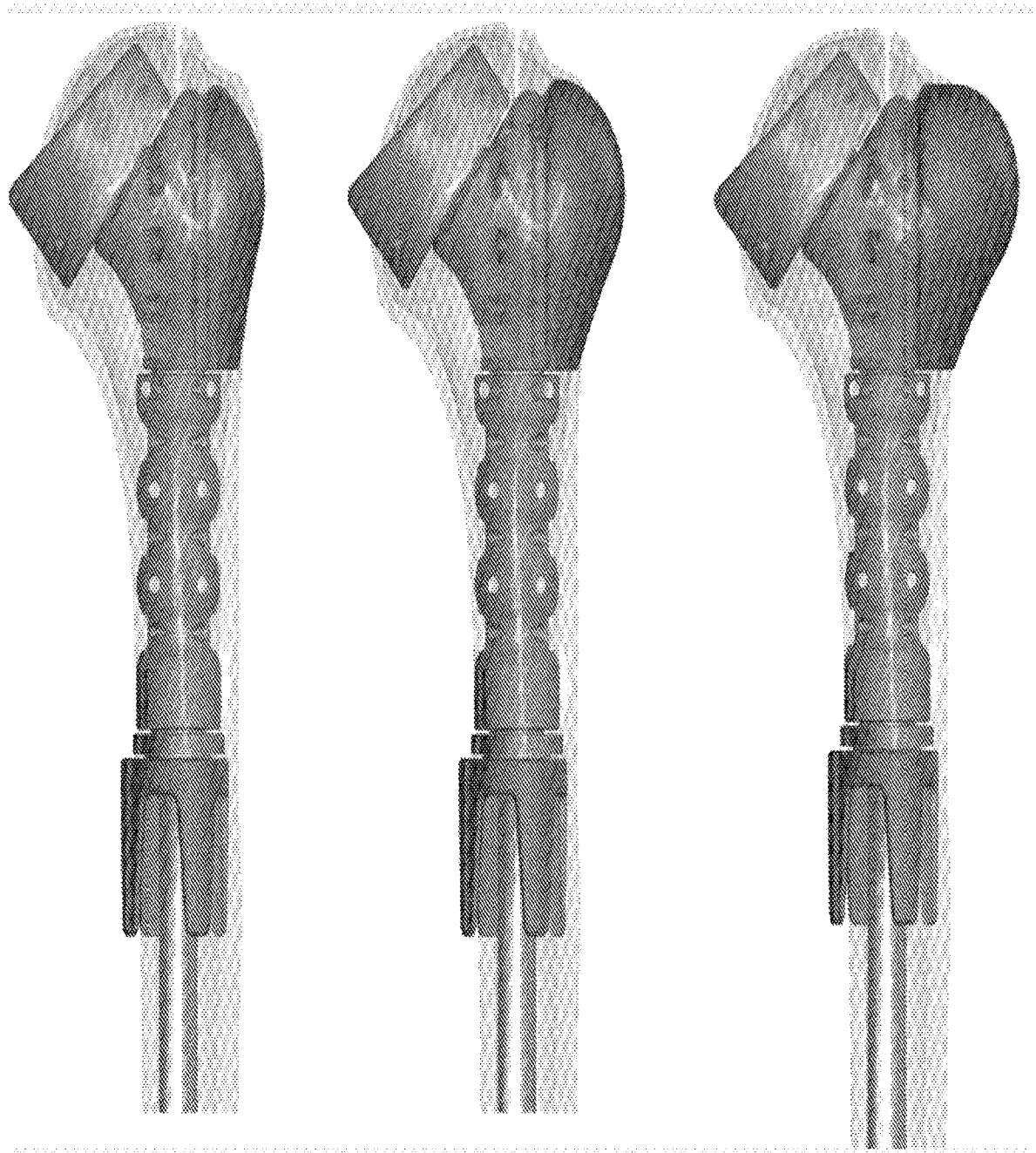
FIGS. 18A-18C show the devices of FIGS. 13A-13C overlaid with a humeral bone. In these images the anatomic tuberosity positions are restored.
Figures 19A, 19B, 19C, 19D, 19E, 19F, 19G, 19H:
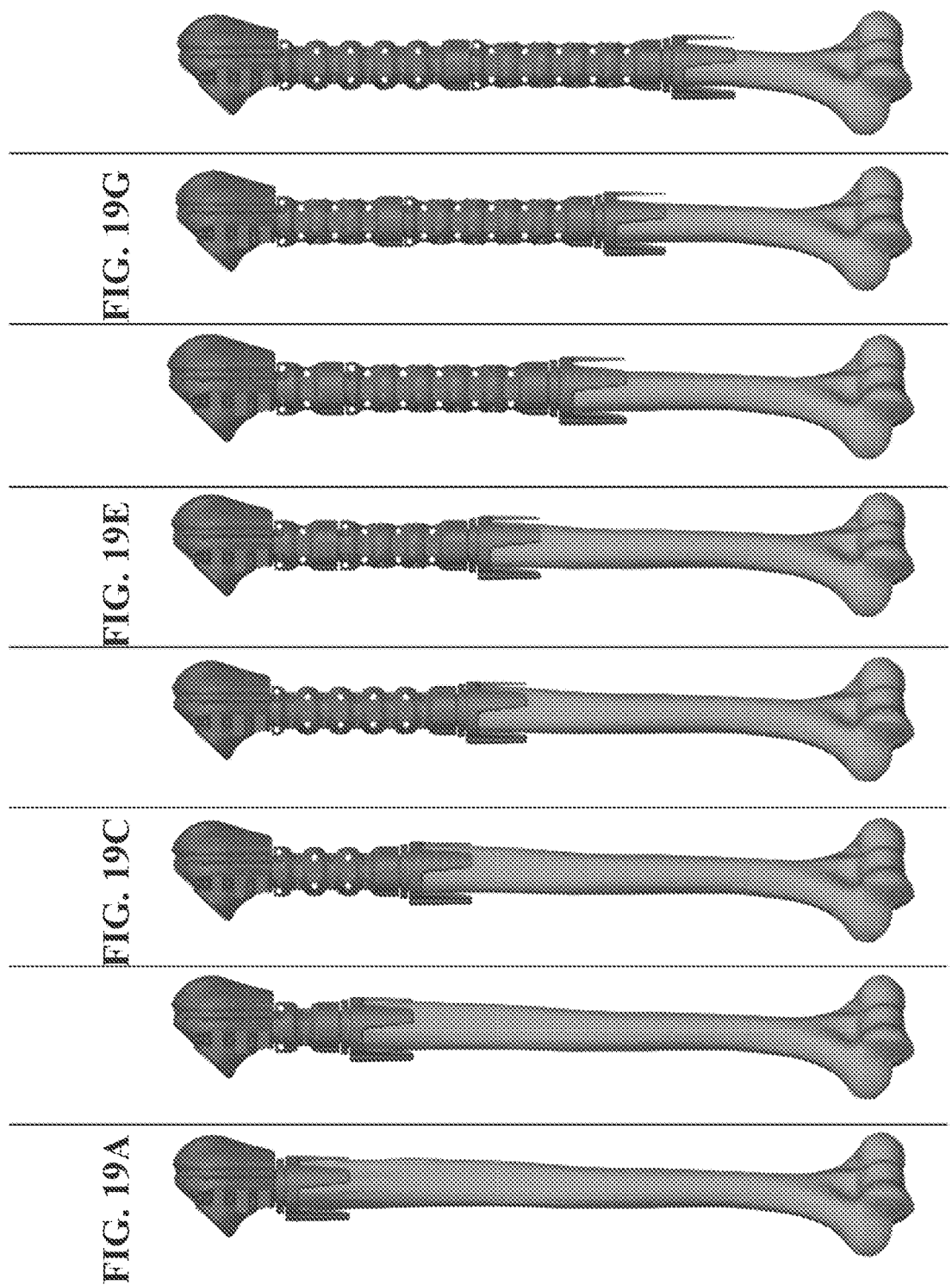
FIGS. 19A-19H show the prosthetic device of FIG. 6 with no middle segment component (FIG. 19A), with different length middle segment components (FIGS. 19B-19D) or with two or more middle segment components (FIGS. 19E-19H) for use in surgical neck resection or oncology applications.

FIGS. 18A-18C show the devices of FIGS. 13A-13C overlaid with a humeral bone. In FIG. 18A the anatomic tuberosity position is restored. In FIGS. 18B and 18C, the tuberosity position is lateralized to facilitate greater deltoid wrapping around each tuberosity and more joint compression by the deltoid. The ability to selectively choose a tuberosity of varying thickness permits the surgeon to better tension the joint in a primary or reverse shoulder arthroplasty by changing the amount that the deltoid wraps around the greater tuberosity which increases the compression of the proximal humerus into the glenoid. Improved deltoid wrapping may also improve the cosmetic concern with reverse shoulder arthroplasty.

FIGS. 19A-19H show the prosthetic device of FIG. 6 with no middle segment component (FIG. 19A), with different length middle segment components (FIGS. 19B-19D) or with two or more middle segment components (FIGS. 19E-19H) for use in surgical neck resection or oncology applications. The device 100 can include more than one middle segment to accommodate varying humeral osteotomies (as would occur in oncology applications in which the humeral bone is resected and the soft tissue would need to be reattached). For a surgical neck resection, the device 100 may include a 2 piece design including a proximal segment and a tuberosity (FIG. 19A), wherein the proximal segment engages with a humeral stem. For an oncology application, in which the humeral bone is resected between the surgical neck and deltoid tuberosity, the device 100 may include at least a 3 piece design including a proximal segment, a tuberosity and one or more middle segments (FIGS. 19B-19D), wherein the final middle segment engages with the humeral stem. For an oncology application, in which the humeral bone is resected below the deltoid tuberosity, the device 100 may include at least a 4 piece design including a proximal segment, a tuberosity and two or more middle segments (FIGS. 19E-19H), wherein the final middle segment engages with the humeral stem.

Figure 20:
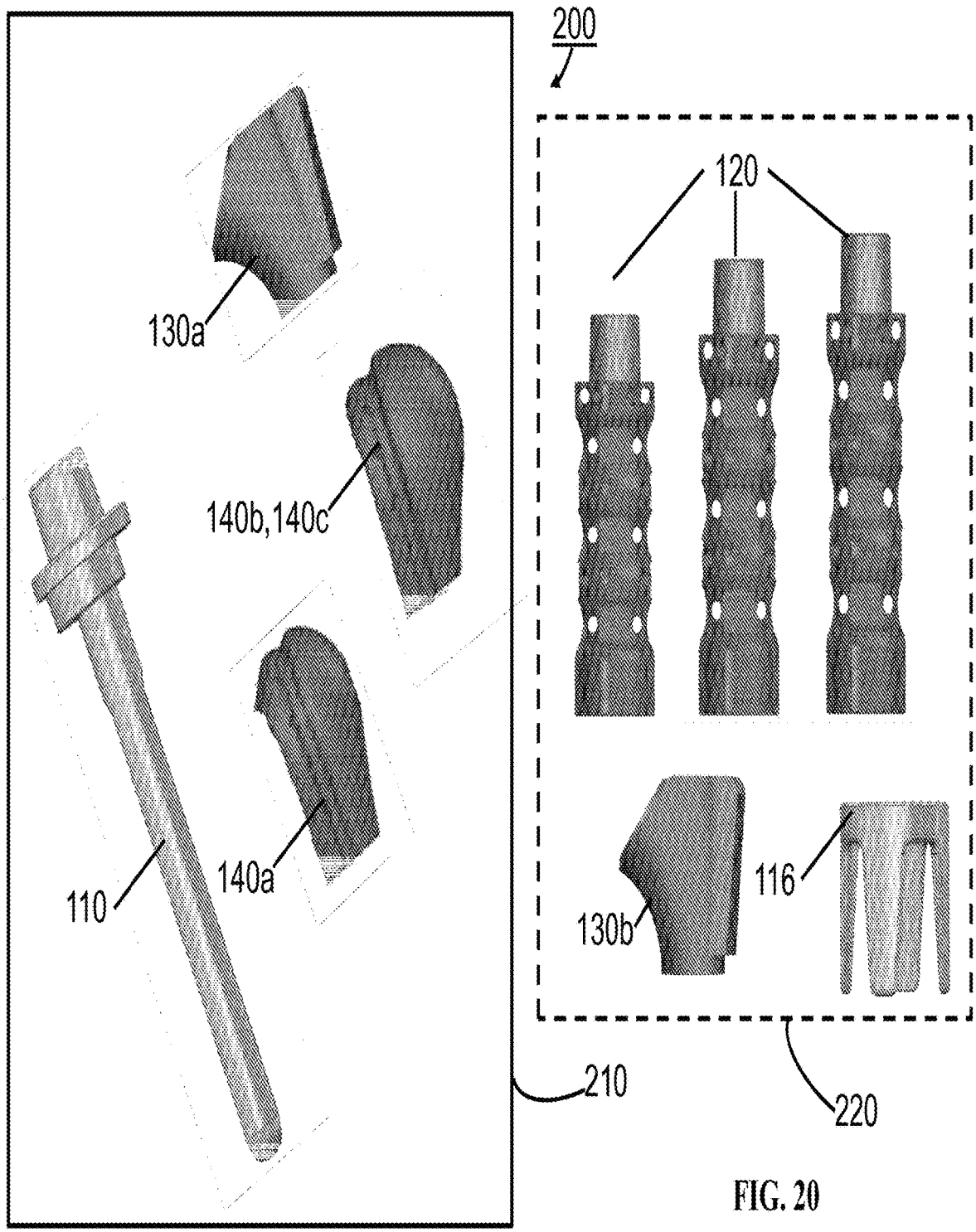
FIG. 20 shows an embodiment of a kit of the present invention.

FIG. 20 shows an embodiment of a kit 200 of the present invention. Kit 200 includes humeral stem 110 having a central longitudinal axis and configured to attach to a resected bone; first tuberosity component 140*a* having a first thickness relative to the central longitudinal axis of the humeral stem 110; a second tuberosity component 140*b* or 140*c* having a second thickness relative to the central longitudinal axis of the humeral stem 110, wherein the first thickness of the first tuberosity component 140*a* is different that the second thickness of the second tuberosity component 140*b* or 140*c*; and proximal segment 130*a* configured to engage both the first tuberosity component 140*a* and the second tuberosity component 140*b* or 140*c*. The components of the kit 200 are arranged in a case 210 that conveniently allow kit components to be readily identifiable and available during a surgical procedure. In an embodiment, the first thickness of the first tuberosity component is at least 20 mm relative to the central axis of the humeral stem, and the second thickness of the second tuberosity component is at least 20 mm relative to the central axis of the humeral stem, as explained in more detail with respect to FIGS. 13A-13C. In an embodiment, kit 200 further includes distal fixation ring 116, a second proximal segment 130*b*, and one or more middle segments 120 which can be arranged in case 210 or separate case 220.

Figure 21:
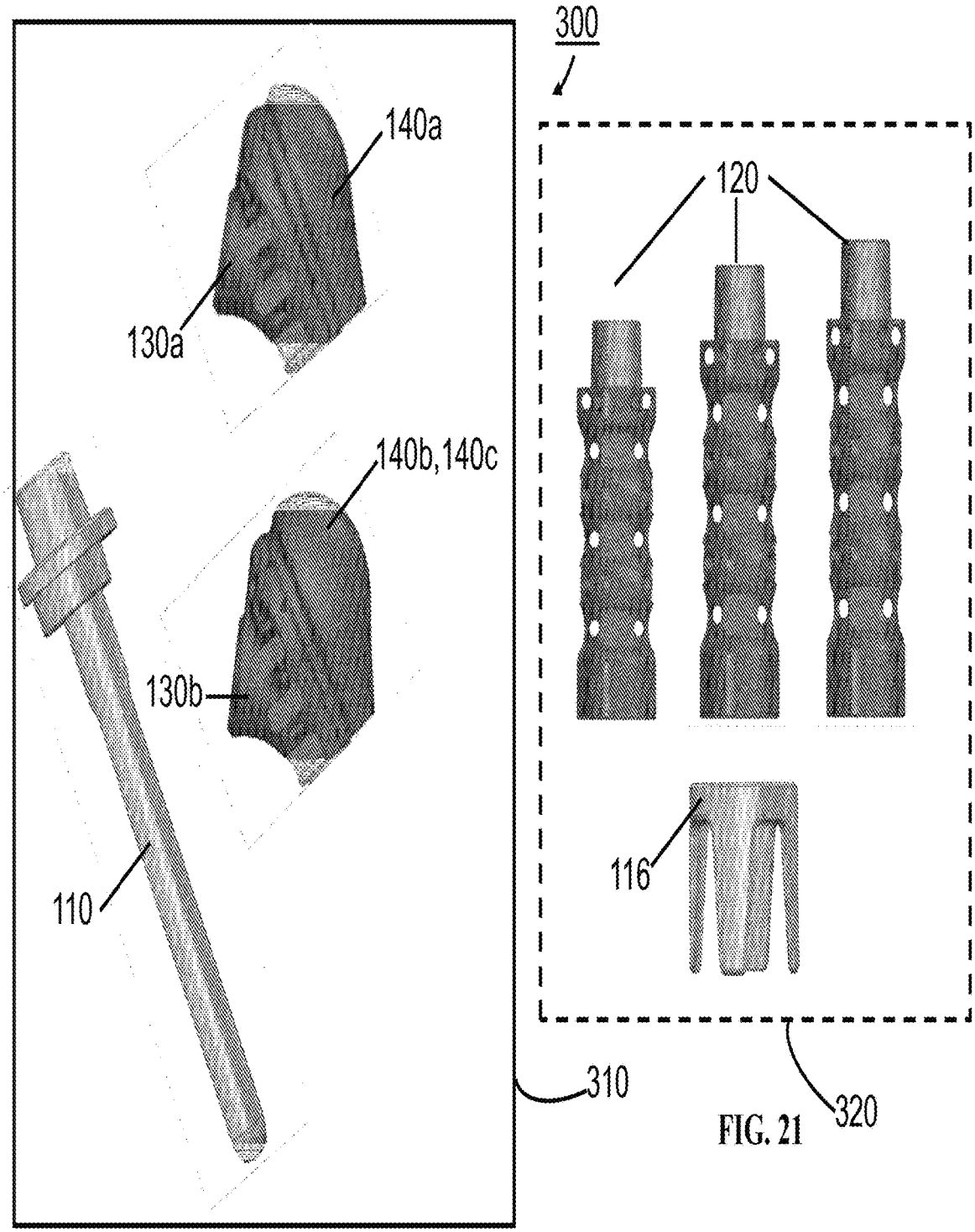
FIG. 21 shows an embodiment of a kit of the present invention.

FIG. 21 shows an embodiment of a kit 300 of the present invention. Kit 300 includes humeral stem 110 having a central longitudinal axis and configured to attach to a resected bone; a first proximal segment 130*a* having an integral first tuberosity component 140*a* (the proximal segment 130*a* and the tuberosity component 140*a* are one-piece) with a first thickness relative to the central longitudinal axis of the humeral stem 110; and a second proximal segment 130*b* having an integral second tuberosity component 140*b* or 140*c* (the proximal segment 130*b* and the second tuberosity component 140*b* or 140*c* are one-piece) with a second thickness relative to the central longitudinal axis of the humeral stem 110, wherein the first thickness of the first tuberosity component 140*a* is different that the second thickness of the second tuberosity component 140*b* or 140*c*. The components of the kit 300 are arranged in a case 310 that conveniently allow kit components to be readily identifiable and available during a surgical procedure. In an embodiment, the first thickness of the first tuberosity component is at least 20 mm relative to the central axis of the humeral stem, and the second thickness of the second tuberosity component is at least 20 mm relative to the central axis of the humeral stem, as explained in more detail with respect to FIGS. 13A-13C. In an embodiment, kit 300 further includes distal fixation ring 116 and one or more middle segments 120 which can be arranged in case 310 or separate case 320.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A device, comprising:
   a proximal component of a humeral side of a shoulder prosthesis,
   wherein the proximal component has a proximal end, a distal end, a medial portion and a lateral portion,
   wherein the medial portion of the proximal component is configured to connect to an articulating component of a humeral side of a shoulder prosthesis when the humeral side of the shoulder prosthesis is fully assembled, the articulating component having an articular surface,
   wherein a volume of the proximal component is configured to wrap a patient's deltoid muscle around the lateral portion of the proximal component to a desired degree by lateralizing where the patient's deltoid muscle wraps around the device to achieve a desired wrapping angle, wherein the lateral portion of the proximal component is configured to allow the patient's deltoid muscle to slide over an outer surface of the lateral portion of the proximal component when the patient's deltoid muscle wraps around the device in a manner such that the patient's deltoid muscle is allowed to move freely with respect to the proximal component, wherein the outer surface of the lateral portion of the proximal component is configured to prevent abrasion or damage to the deltoid muscle as it slides over the outer surface of the lateral portion of the proximal component, wherein the outer surface of the lateral portion of the proximal component has a curvature that is discontinuous with a curvature of the articular surface of the articulating component of the humeral side of the shoulder prosthesis when the proximal component connects to the articulating component of the humeral side of the shoulder prosthesis when the humeral side of the shoulder prosthesis is fully assembled.

2. The device of claim 1, further comprising:
a humeral stem having a central longitudinal axis, a proximal end, and a distal end, the humeral stem configured to attach to a resected bone.

3. The device of claim 2, wherein the proximal component is configured to lockingly attach to the proximal end of the humeral stem.

4. The device of claim 2, further comprising a fixation ring coupled to the humeral stem.

5. The device of claim 4, wherein the fixation ring is configured to modularly attach to the humeral stem.

6. The device of claim 2, further comprising at least one middle segment connecting the humeral stem to the proximal component.

7. The device of claim 6, wherein the at least one middle segment comprises a plurality of middle segments configured to modularly attach the humeral stem to the proximal component.

8. The device of claim 6, further comprising a fixation ring coupled to the humeral stem.

9. The device of claim 8, wherein the fixation ring is configured to couple modularly to the humeral stem.

10. The device of claim 1, further comprising the articulating component.

11. The device of claim 10, wherein the articulating component is configured to lockingly attach to the proximal component.

12. The device of claim 1, wherein the medial portion and the lateral portion are integrally formed with one another.

13. The device of claim 1, wherein the medial portion and the lateral portion are modularly attached to one another.

14. The device of claim 1, further comprising at least one middle segment extending from the distal end of the proximal segment, wherein the at least one middle segment is configured to be coupled to a humeral stem.

15. The device of claim 14, wherein the at least one middle segment is configured to lockingly attach to the proximal segment.

16. The device of claim 1, wherein the proximal component includes suture bores for soft tissue fixation.

17. The device of claim 1, wherein the outer surface of the lateral portion of the proximal component is a polished surface configured to prevent abrasion or damage to the deltoid muscle as it slides over the outer surface of the lateral portion of the proximal component.

18. The device of claim 1, wherein the outer surface of the lateral portion of the proximal component further comprises a lower potion.

19. A kit, comprising:
a plurality of proximal components of a humeral side of a shoulder prosthesis,
wherein each proximal component has a proximal end, a distal end, a medial portion and a lateral portion,
wherein the medial portion of each proximal component within the plurality is configured to connect to an articulating component of a humeral side of a shoulder prosthesis when the humeral side of the shoulder prosthesis is fully assembled, the articulating component having an articular surface,
wherein a volume of each proximal component is configured to wrap a patient's deltoid muscle around the lateral portion of the proximal component to a desired degree by lateralizing where the patient's deltoid muscle wraps around the device to achieve a desired wrapping angle,
wherein the lateral portion of each proximal component is configured to allow the patient's deltoid muscle to slide over an outer surface of the lateral portion of the proximal component when the patient's deltoid muscle wraps around the device in a manner such that the patient's deltoid muscle is allowed to move freely with respect to the proximal component,
wherein the outer surface of the lateral portion of each proximal component is configured to prevent abrasion or damage to the deltoid muscle as it slides over the outer surface of the lateral portion of the proximal component,
wherein the outer surface of the lateral portion of each proximal component has a curvature that is discontinuous with a curvature of the articular surface of the articulating component of the humeral side of the shoulder prosthesis when the proximal component connects to the articulating component of the humeral side of the shoulder prosthesis when the humeral side of the shoulder prosthesis is fully assembled.

20. The kit of claim 19, wherein each individual proximal component within the plurality has a different volume to any other individual proximal component within the plurality.

21. The kit of claim 19, wherein the proximal components are configured to allow a surgeon to selectively optimize muscle moment arm, muscle tensioning and muscle stability.

22. The kit of claim 19, wherein the proximal components include suture bores for soft tissue fixation.

23. The kit of claim 19, wherein the outer surface of the lateral portion of each proximal component further comprises a lower potion.

24. The kit of claim 19, wherein the medial portion of each proximal component and the lateral portion of each proximal component are modularly attached to one another.

25. The kit of claim 19, wherein the outer surface of the lateral portion of each proximal component is a polished surface configured to prevent abrasion or damage to the deltoid muscle as it slides over the outer surface of the lateral portion of the proximal component.

26. A kit, comprising:
a plurality of medial portions of a proximal component of a humeral side of a shoulder prosthesis,
wherein each medial portion within the plurality is configured to connect to an articulating component of the humeral side of the shoulder prosthesis when the humeral side of the shoulder prosthesis is fully assembled, the articulating component having an articular surface;

a plurality of lateral portions of the proximal component of the humeral side of the shoulder prosthesis,
- wherein a selected one the plurality of lateral portions can be joined to a selected one of the plurality of medial portions to form the proximal component of the humeral side of the shoulder prosthesis, wherein the proximal component has a proximal end and a distal end;
- wherein the volume of each lateral portion is configured to wrap a patient's deltoid muscle around the lateral portion to a desired degree by lateralizing where the patient's deltoid muscle wraps around the humeral side of the shoulder prosthesis to achieve a desired wrapping angle,
- wherein each lateral portion is configured to allow the patient's deltoid muscle to slide over an outer surface of the lateral portion when the patient's deltoid muscle wraps around the humeral side of the shoulder prosthesis in a manner such that the patient's deltoid muscle is allowed to move freely with respect to the proximal component of the shoulder prosthesis,
- wherein the outer surface of each lateral portion of each proximal component is configured to prevent abrasion or damage to the deltoid muscle as it slides over the outer surface of the lateral portion, and
- wherein the outer surface of each lateral portion has a curvature that is discontinuous with a curvature of the articular surface of the articulating component of the humeral side of the shoulder prosthesis when the proximal component connects to the articulating component of the humeral side of the shoulder prosthesis when the humeral side of the shoulder prosthesis is fully assembled.

* * * * *